(12) United States Patent
Kenar et al.

(10) Patent No.: US 7,875,262 B2
(45) Date of Patent: Jan. 25, 2011

(54) AQUEOUS STARCH-OIL DISPERSIONS HAVING IMPROVED UV STABILITY AND ABSORBING ABILITY

(75) Inventors: James A. Kenar, East Peoria, IL (US); David L. Compton, Peoria, IL (US); Frederick C. Felker, Morton, IL (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 456 days.

(21) Appl. No.: 11/584,905

(22) Filed: Oct. 23, 2006

(65) Prior Publication Data

US 2007/0140995 A1   Jun. 21, 2007

Related U.S. Application Data

(60) Provisional application No. 60/752,561, filed on Dec. 21, 2005.

(51) Int. Cl.
*A61K 8/00* (2006.01)
*A61K 8/18* (2006.01)
*A61Q 17/04* (2006.01)

(52) U.S. Cl. .................................. 424/59; 424/70.9
(58) Field of Classification Search ............. 424/59, 424/70.9
See application file for complete search history.

(56) References Cited

U.S. PATENT DOCUMENTS

| 5,663,213 | A | | 9/1997 | Jones et al. |
| 5,882,713 | A | * | 3/1999 | Eskins et al. ................ 426/578 |
| 6,346,236 | B1 | * | 2/2002 | Compton et al. .............. 424/60 |
| 6,384,104 | B1 | | 5/2002 | Chang et al. |
| 7,163,673 | B2 | * | 1/2007 | Compton et al. .............. 424/59 |
| 2003/0031722 | A1 | * | 2/2003 | Cao et al. ................... 424/493 |
| 2004/0258743 | A1 | | 12/2004 | Compton et al. |

* cited by examiner

*Primary Examiner*—Johann R Richter
*Assistant Examiner*—Luke E Karpinski
(74) *Attorney, Agent, or Firm*—John Fado; Randall E. Deck; Lesley Shaw (57) ABSTRACT

A delivery system for UV-protective sunscreen agents, antioxidants, skin care agents, cosmetics and the like comprising feruloylated acylglycerols (FAG) and other cinnamate-modified vegetable oils (CMVO) incorporates the agents into starch-based composites. These composites permit the use of a lower level of CMVO for comparable UV protection than if the CMVO were used alone.

18 Claims, 4 Drawing Sheets

AQUEOUS STARCH-OIL DISPERSIONS HAVING IMPROVED UV STABILITY AND ABSORBING ABILITY

CROSS-REFERENCE TO RELATED APPLICATION

This application claims the benefit under 35 U.S.C. 1.19(e) of U.S. provisional patent application No. 60/752,561, filed Dec. 21, 2005, the contents of which are incorporated by reference herein.

This invention is related to commonly-assigned Ser. No. 10/462,882 entitled "Novel Sunscreen Reagents from Hydroxy-Substituted Acylglycerides" filed on Jun. 17, 2003 and published on Dec. 23, 2004, as US 2004-0258743 (Compton et al.), and to commonly-assigned Ser. No. 10/463,491 entitled "Novel Sunscreen Reagents from Unsaturated Waxes and Triglycerides" filed on Jun. 17, 2003, and published on Dec. 23, 2004, as US 2004-0258635 (Harry-O'Kuru et al.), both herein incorporated by reference.

BACKGROUND OF THE INVENTION

1. Field of the Invention

This invention relates to delivery of phenol-modified vegetable oils useful as UV-protective sunscreen agents, antioxidants, skin care agents, cosmetics and the like in starch-based compositions having a continuous aqueous phase and a dispersed oil phase.

2. Description of the Prior Art

An all natural sunscreen active ingredient has been derived from two natural plant components, ferulic acid and soybean oil (SBO) (Compton et al., U.S. Pat. No. 6,346,236). The "green", enzymatic transesterification between the ethyl ester of ferulic acid, ethyl ferulate (EF), and soybean oil produces a mixture of feruloylated acylglycerols (FAG) that comprise at least monoacyl- and diacyl glycerols that are the major constituents of an all natural, soy-based sunscreen (Laszlo et al., *Green Chem.* 2003, 5, 382-386). Ferulic acid is a phenolic compound (a member of the cinnamic acid family) that is found esterified in most higher plants with hemicelluloses, lignins, and phytosterols. Thus, ferulic acid is a common component of the human diet. The feruloyl moiety of the FAG has a strong ultraviolet A (UVA) and B (UVB) absorbance while the acylglycerol portion of the FAG provides water resistance (Compton et al., U.S. Pat. No. 6,346,236). These characteristics make FAG a suitable, all natural replacement for commercially used petroleum-based sunscreen active ingredients.

An obvious use of FAG is as a broad UV-absorbing active ingredient in sunscreens, health and beauty aids, and daily wear cosmetics. Formulation and commercialization of FAG into such products is currently being investigated. However, less obvious but important applications also include using FAG as an adjuvant to provide natural UV protection in paints, coatings, and insecticidal and herbicidal biocontrol agents. As most insecticidal and herbicidal agents are aqueous based, it is necessary to formulate water-based systems containing FAG that allow sprayable, uniform films to be prepared. Initial trials to emulsify FAG into aqueous-based agricultural spray formulations using conventional surfactants have met with limited success. The resultant films are non-uniform and do not provide the even coverage needed in agricultural adjuvant applications. An improved, more reliable method for incorporating FAG into aqueous-based agricultural sprays is needed.

An interesting class of highly stable water dispersible starch-lipid composites has recently been developed at our facilities by co-jet cooking starch with lipophilic materials such as vegetable oils under excess steam conditions (Eskins et al., U.S. Pat. No. 5,676,994; Eskins et al., U.S. Pat. No. 5,882,713; Fanta et al., *Carbohydr. Polym.*, 1999, 39, 25-35). The resulting composites can readily contain up to 50% lipophilic material relative to the starch component and are water dispersible over a wide range of dilution. Previous publications (Fanta et al., *Carbohydr. Polym.*, 1995, 28, 171-175; Fanta et al., *Carbohydr. Polym.*, 1999, 39, 25-35; Eskins et al., *Carbohydr. Polym.*, 1996, 29, 233-239) describe the preparation, properties and microscopic analysis of these composites and show the composites to consist of lipid droplets having typical diameters in the 1-10 µm range coated with a thin film of firmly bound starch at the oil-water interface. The water dispersed oil-starch composites can be drum dried to produce oil microencapsulated in starch flakes that are easily reconstituted in water to again form smooth, stable dispersions. These starch-oil composites provide an ideal method to carry lipophilic components into aqueous systems without the need for additional emulsifiers, stabilizers, or surfactants.

SUMMARY OF THE INVENTION

We have now devised a delivery system for FAG and other cinnamate-modified vegetable oils (CMVO) useful as UV-protective sunscreen agents, antioxidants, skin care agents, cosmetics and the like in which the agents are incorporated into starch-based composites. The resultant products are hereafter referred to as "SB-CMVO" composites. Those composites in which the CMVO is FAG are hereafter referred to as "SB-FAG".

It is an object of this invention to formulate CMVO into a starch-based matrix that would be easily dispersible in aqueous media while maintaining the UV absorbing efficacy of the CMVO.

In addition, it is an object of the invention to provide a delivery system for CMVO that unexpectedly permits the use of a lower level of CMVO for comparable UV protection than if the CMVO were used alone.

It is also an object of the invention to produce sunscreen agents and a delivery system that have the advantage of being synthesized from natural materials, while providing value-added use for vegetable oils and starch.

Other objects and advantages of this invention will become readily apparent from the ensuing description.

BRIEF DESCRIPTION OF THE FIGURES

FIG. 4A: (Δ) SB-SBO composites (51%, w/w oil/starch), 1.74 mg/cm$^2$; (○) FAG, 0.23 mg/cm$^2$; (□) SB-FAG composites (51%, w/w oil/starch), 0.33 mg/cm$^2$; FIG. 4B: (Δ) SB-FAG composites (51%, w/w oil/starch), 1.74 mg/cm$^2$; (○) FAG, 0.64 mg/cm$^2$; (□) SB-FAG composites (52%, w/w oil/starch), 0.59 mg/cm$^2$.

DETAILED DESCRIPTION

The compounds of this invention, hereafter referred to as "active agents" consist of one or more acylglycerols (e.g. triglycerides) wherein one or more of the acyl substituents have been replaced with a cinnamate moiety selected from the group of feruloyl, coumaroyl, sinapoyl, and o-methylsinapoyl moieties (Embodiment I); or wherein one or more of the acyl substituents are modified with one or more cinnamate moieties, selected from the group of feruloyl, coumaroyl, sinapoyl, and o-methylsinapoyl moieties (Embodiment II). Thus, these compounds are generally characterized by Formula 1:

Formula 1 wherein at least one of $R_1$, $R_2$, or $R_3$ is a feruloyl, coumaroyl, sinapoyl, or o-methylsinapoyl moiety (Embodiment I) or an acyl moiety modified with one or more feruloyl, coumaroyl, sinapoyl, or o-methylsinapoyl moiety (Embodiment II). For either embodiment, the remaining position(s) ($R_1$, $R_2$ and/or $R_3$) can be any combination of C2-C26 acyl moieties, C1-C26 aliphatic moieties, and hydrogen.

The natural isomers of plant phenols are trans at the olefinic group; however, it is envisioned that the feruloyl, coumaroyl, sinapoyl, and o-methylsinapoyl moieties used herein could also be cis. Structures of the various cinnamic acids are given in Formula 2, below.

Structures of Various Cinnamic Acids

Formula 2

$R_4$, $R_5$, $R_6$=H cinnamic acid
$R_4$=H; $R_5$=OH; $R_6$=OCH$_3$ ferulic acid
$R_4$, $R_6$=OCH$_3$; $R_5$=OH sinapic acid
$R_4$, $R_6$=H; $R_5$=OH coumaric acid
$R_4$, $R_5$, $R_6$ OCH$_3$ o-methylsinapic acid Preferably the source acylglycerol is a triglyceride, particularly a natural vegetable oil. These oils may have fatty acid moieties ranging in length from C2-C26, preferably C12-C26 and most preferably, C16-C22. The fatty acid moieties (residues) on a given acylglyceride molecule may have varying degrees of saturation, from completely saturated (defined herein for purposes of this application to include hydroxyl-substituted) to tri-unsaturated. When the products of the invention are intended for use in cosmetic formulations, it is preferred to select vegetable oils that are aromatically pleasing, particularly those having a relatively low level of linolenic acid, for example. Of course, synthetic triglycerides, such as triolein, could also be used as the starting material.

For Embodiment I wherein at least one of $R_1$, $R_2$, or $R_3$ is a feruloyl, coumaroyl, sinapoyl, or o-methylsinapoyl moiety, exemplary source oils include soybean oil, corn oil, sunflower seed oil, high-oleic sunflower seed oil, canola oil, safflower oil, cuphea oil, jojoba oil, coconut oil, palm kernel oil, and the like.

An exemplary active agent in accordance with Embodiment I is shown by Formula 3:

Formula 3 wherein $R_2$ and $R_3$ are each independently selected from OH and a C2-C24 fatty acid moiety.

These compounds are most readily produced in a lipase-catalyzed transesterification reaction between a glyceride and a simple acyl ester of ferulic or coumaric acid substantially as described by Compton et al. in U.S. Pat. No. 6,346,236, herein incorporated by reference. C1-C10 acyl esters of ferulic or coumaric acid, and particularly C2-C8 acyl esters would be advantageously used in the transesterification reaction.

For Embodiment II, where the acyl chain itself is to be modified with a cinnamate moiety as discussed above, it is necessary that at least some of the fatty acid moieties in a given oil sample are hydroxy-substituted in order to provide sites of esterification by the selected cinnamic acid. Exemplary natural oils that are naturally hydroxylated and are useful as starting materials for this embodiment of the invention include lesquerella oil (high in lesquerolic acid) and castor oil (high in ricinoleic acid) wherein the hydroxy moiety occurs on C14 or C12, respectively. Other oils useful as starting materials for this embodiment would be synthetically-derived hydroxylated oils, such as hydroxylated milkweed oil described in the published application of Harry-O'Kuru et al. (US 2004-0258635), supra.

An exemplary active agent in accordance with Embodiment II is shown by Formula 4:

Formula 4

Feruloyl-Lesquerella ester

These compounds are most readily produced in a reaction between hydroxy-containing acylglycerides and ferulic, coumaric, sinapic, and o-methylsinapic acid, the structures of which are shown, above, substantially as described in U.S. Patent Application Publication No. 2004/0258743, herein incorporated by reference. Esterification of acid moieties with the hydroxy-substituted fatty acid moiety is optimally conducted in the absence of oxygen, such as in vacuo or under nitrogen, and without the use of a catalyst or a solvent. The fatty acid or acylglyceride is reacted with ferulic, coumaric, sinapic or o-methylsinapic acid at a temperature ranging from about 150° C. to about 250° C. for a period of time ranging from about 12 to 72 hours.

The active agents of this invention are characterized by the properties of having the UV absorptivity of a cinnamate ester and the water-insoluble properties of a lipid, thereby rendering them useful as active agents for the skin that do not readily wash off with water. The UV absorbance of these products extends from about 280 nm to about 350 nm, and they are particularly effective in absorbing UV in the range of about 310 nm to about 350 nm. This is predominantly in the UVA range, but also covers part of the UVB range. For additional UVB protection, the subject compounds may be formulated with other active agents as discussed below.

The active agents of this invention are incorporated as water-insoluble/water immiscible materials into starch-based composites essentially as described in U.S. Pat. Nos. 5,676,994 and 5,882,713, both herein incorporated by reference in their entireties. The composites are preferably prepared from unmodified starches obtained from cereal grains, such as corn, wheat and rice or from root crops such as potato and tapioca. Although any available starch variety is suitable for the preparation of these compositions, the skilled artisan will recognize that differences in branching and molecular weight can cause differences in physical properties between the many known varieties of starch. This, in turn, can lead to differences in the properties of the final compositions of matter. An unmodified starch is one that has not been altered by chemical treatment or reduced in molecular weight by reaction with acids or enzymes. Modified starches may be used to prepare the compositions of this invention, if certain properties are desired that are not obtainable with unmodified starches. Starches from a particular plant variety having amylose and amylopectin components in varying proportions may also be used, for example, waxy cornstarch, having an amylose content of essentially 0%, and cornstarch having an amylose content greater than the 25% that is characteristic of starch from dent corn varieties. In the most preferred embodiments of this invention, the amylose content of the starch is less than 35%. Although starch is preferably used in the preparation of the compositions of this invention, cereal flour can also be used. Cereal flour is a finely ground meal obtained by the milling of corn, wheat, oats or other cereal grains and consists essentially of the starch and protein components of the endosperm portion of the grain.

Compositions of the invention are prepared from starch and active agent in amounts ranging from about 5 parts to about 900 parts of agent, by weight, per 100 parts of starch (that is, the active agent is in an amount of about 5-90% of the combined starch/active agent composition on a dry weight basis). Although it is obvious that fewer than 5 parts of active agent per 100 parts of starch can also be used, it is questionable whether, for most applications, the presence of the agent in such small quantities will lead to sufficient improvements in the properties of the starch-containing composition to justify the costs associated with processing. The upper limit for the amount of agent in the final composite is dictated by the point at which the agent begins to separate from the recovered product. For example, a dried composition having an outwardly oily character might be objectionable for many applications since it would be difficult to grind or mill such a product to a small particle size. Furthermore, a particulate composition having an outwardly oily character would tend to cake and be resistant to flow. Typically, the upper practical limit of active agent would not exceed 65 parts agent per 100 parts by weight of the starch (40%). Preferred compositions have a starch/CMVO weight ratio varying between 1:1 and 9:1, more preferably in the range of 1:1 to 3:2, and even more preferably in a ratio of about a 1:1.

One method for preparing the compositions of this invention is to first prepare a blend of starch, active agent and water by rapidly stirring the components of the mixture together at or near room temperature. When the stirrer is stopped, these mixtures tend to separate almost immediately into an upper phase, that consists substantially of active agent, and a lower phase that consists substantially of starch and water. Therefore, it is desirable to quickly feed the dispersion into the cooker in order to minimize such separation. In an alternative embodiment of the invention referred to as the "twice cook" method, the dispersion expelled from the cooker is recycled back into the cooker in order to more homogeneously disperse the active agent into the aqueous starch phase.

The pH of the aforementioned dispersion is typically in the 3.5-7 range and may be optionally adjusted to any range desired by the addition of an acid or base, typically hydrochloric acid or sodium hydroxide. The starch concentration in water is typically in the range of about 10-15% by weight, although concentrations as high as about 35% by weight may be used. The upper limit for the concentration of starch in water is dictated only by the high viscosity of the cooked dispersion of starch, active agent and water. Starch concentrations lower than about 10-15% may also be used; however, with lower solids levels, greater amounts of water must be removed during product recovery, and the expense associated with the drying process will thus be increased. In the preferred embodiment of the invention, agents, such as salt, for promoting the precipitation of the starch are not used. Such agents have a tendency to interfere with the physical and functional properties of the products.

Figure 1:
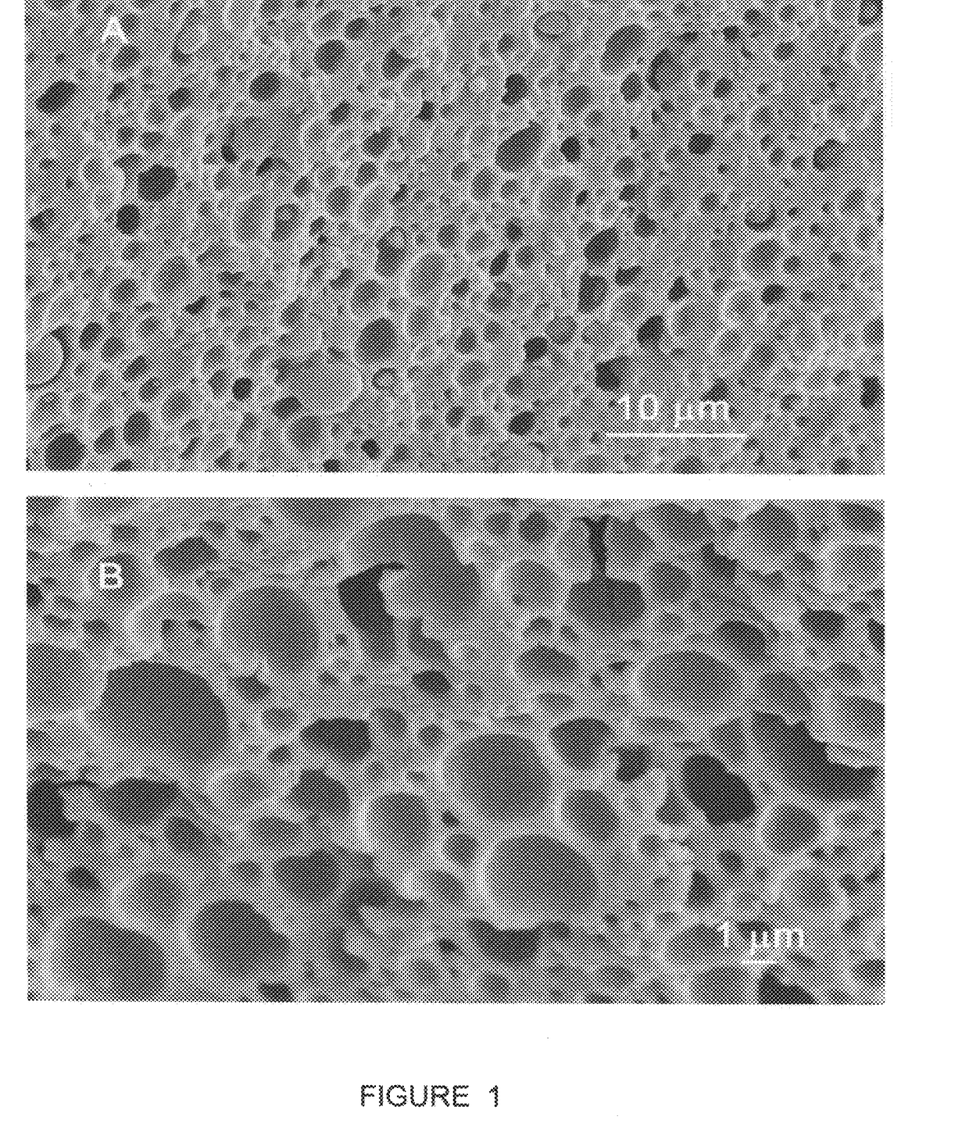
FIGS. 1A and 1B are scanning electron micrographs of ethanol extracted dried SB-FAG films fractured to expose the internal structure of the film at ×2000 magnification and at ×5000 magnification, respectively.

The cooking is preferably carried out with an excess steam jet cooker (Klem et al., *Pulp & Paper*, 1981, 55, pages 98-103) under conditions necessary to attain complete disruption of starch granules and complete solution in water of both the amylose and amylopectin components of starch. The effects of jet cooking on the physical and functional properties of starch are discussed by Dintzis et al. (*J. Rheol.*, 1995, 39(6): 1483-1495) and in Dintzis et al. (*J. Appl. Polymer Sci.*, 1996, 62: 749-753), both herein incorporated by reference. We believe that the unique physical properties of the products of this invention are due not only to the fact that starch is rendered substantially water-soluble by the cooking operation, but also to the partial molecular breakdown of starch and to the intense mixing and turbulence encountered by the dispersion of starch, active agent and water as it is subjected to the excess steam jet cooking process. These turbulent and high shear cooking conditions, coupled with the elevated temperatures and pressures used for cooking, constitute a unique processing system which not only disperses the active agent in the aqueous starch solution but also provides a dispersion of starch, active agent and water that will not phase-separate, even after prolonged standing. The term "dispersion" in the context of this invention refers to micron-sized droplets of active agent uniformly entrapped within a starch or starch-water matrix. It is surprising that stable dispersions of this nature, wherein domains of the active agent as the discontinuous phase are substantially uniformly dispersed throughout the continuous aqueous starch phase, can be obtained without the addition of an external emulsifying agent. The expression "substantially uniformly dispersed" is intended to mean that the dispersion of oil in starch is homogeneous. For example, a random sample of a preparation, on a scale of a few milligrams, would contain approximately the same proportion of active agent to starch as any other sample of that size. FIG. 1 illustrates the products of the invention on a microscopic scale. As evident in the micrograph, droplets of oil (appearing as voids left thereby in preparing the material for making the micrograph) appear as large, uniformly dark areas. These droplets constitute the discontinuous phase and are separated from the matrix of solubilized starch constituting the continuous phase by a boundary layer (light gray areas). The expression "external emulsifying agent" is used herein in reference to an agent apart from the principal components themselves, such external emulsifying agents, if used, being intended to promote the emulsification of the active agent in the aqueous starch system. The products of this invention are distinguished from "encapsulated" agents wherein relatively large drops of the discontinuous phase are encased within a protective layer of starch.

Although jet cooking conditions may be varied by one skilled in the art according to the particular starch variety and the particular active agent used, preferred cooking conditions for these compositions are in the range of about 130-150° C. with a steam pressure of about 20-50 psig within the cooker and a pumping rate of about 0.75-2.0 liters per min. Typical conditions are 140° C. with a steam pressure of 40 psig and a pumping rate of 1.1 l/min. Line pressure steam entering the cooker to achieve such conditions would be 65-70 psig. Thus the excess steam flowing through the cooker, over and above that needed to maintain the desired cook temperature, should be at least about 15 psig, and preferably between about 25 and 30 psig. Under these conditions, sufficient turbulence is provided in the cooker to convert the active agent to a microdispersed state. The high steam pressure used during the cooking process is suddenly released as the cooked dispersion exits the jet cooker. This instantaneous pressure release promotes the molecular degradation of the starch and results in an immediate temperature drop of the cooked starch solution to 100° C. or lower. The temperature drop of the solution causes a sharp increase in solution viscosity. This higher viscosity, in turn, is at least responsible for keeping the dispersed droplets of active agent uniformly suspended in the starch-water phase and reduces their tendency to separate and coalesce. The products within the ambit of this invention will be characterized by active agent droplets having a maximum diameter on the order of about 100 microns. Typically, there will be a distribution of active agent droplet sizes, ranging from under one micron to about 30 microns, and most preferably 95% of the active agent droplets will be under 10 microns in size. These active agent droplet sizes can be achieved by appropriate control of the conditions of combining the starch paste and active agent and product recovery. For purposes of this invention, active agent droplets under 10 microns in diameter will be considered as being "micron-size". The amount of active agent used relative to starch, the solids concentration in water and the conditions of cooking are all selected so that the hot, jet cooked dispersion is in the form of a pourable, free-flowing fluid, but having a viscosity significantly higher than that of water itself. Higher line pressures and higher steam pressures within the cooker than those described above will cause a higher level of molecular breakdown of the starch and will thus reduce the ultimate viscosity of the jet cooked dispersion. Steam pressure may thus be varied to alter the physical properties of the final product.

Subsequent to preparing the cooked starch/active agent dispersion, the products of this invention are recovered under conditions which will stabilize the distribution of the active agent droplets in the starch phase. Allowing the dispersion to cool to below the retrogradation temperature prior to drying promotes gelling of the starch and concomitant viscosity increase in the final product. After the material exits the excess steam jet cooker, this cooling occurs very rapidly under atmospheric conditions as previously described. A portion of the active agent is not readily extractable from the dried product with organic solvents, and is characterized as "tightly bound" oil. By slowly stirring the aqueous dispersion during or after cooling, the viscosity of the dispersion becomes significantly higher than when the dispersion remains unstirred.

The skilled artisan in the field of polysaccharide chemistry will appreciate that the pH of the aqueous dispersion of starch and active agent during jet cooking and drying will influence the viscous properties of these compositions when they are used in various end-use applications, such as in lotions, cosmetics, and biocontrol delivery systems. As the pH during processing is lowered, the starch will incur increasing amounts of acid-induced hydrolytic degradation. This will lead to lower viscosities and also perhaps to a reduced tendency toward gel formation. One skilled in the art can thus prepare a variety of different compositions from the same mixture of starch and active agent by simply varying the pH over a wide enough latitude during jet cooking and drying. For most applications, however, a pH within the 5-7 range during processing is preferred.

As previously discussed, the active agent has a tendency to separate from the starch and water in the dispersion prior to cooking. In a variation of the "twice cook" method described above, the blended dispersion of starting components can be stabilized by the addition of product of the invention which has already been recovered. This recycle, or "add-back" stream, can be material which is either obtained directly from the exit of the steam jet cooker, or recovered as ground, dried product. The amount of recycle material in this preferred embodiment should be in excess of about 1% of the dispersion on a dry weight basis in order to have a noticeable effect on the stability of the blend. Typically, the add-back material would constitute 10-25% of the dispersion. The initial dispersion stabilization imparted by the add-back material results in both a higher percentage of the active agent which becomes tightly bound in the starch matrix and also in greater than 95% of the original agent becoming incorporated into the final product. It is by means of this approach that products having 50-70 parts active agent per 100 parts starch, by weight (33-41%), are most easily prepared. The "add-back" embodiment is also useful for encapsulating a second lipid material in addition to the active agent.

In yet another embodiment of the invention, it is contemplated that the active agent is not added until after the aqueous starch dispersion exits from the jet cooker. However, it is critical for the active agent to be added while the starch dispersion is in a non-retrograded form. It is also critical for the active agent to be blended with the dispersion under conditions of high shear and turbulence commensurate with that which occurs within the cooker itself when operated under the conditions described above. A Waring® blender provides a sufficient amount of mechanical shear on a laboratory scale to intimately mix the active agent with the hot starch dispersion. It is envisioned that a colloid mill could also be used for this purpose.

The completely solubilized starch can also be "locked" into a non-retrograded form by drying the material shortly after it exits the jet cooker. It is then possible to redisperse the dried starch in water and introduce active agent under conditions of shear and turbulence, thereby forming a dispersion comparable to that produced by co-cooking the starch and active agent or by adding the active agent just after cooking as described above. It is envisioned that this embodiment would be especially useful for the entrapment of volatile agents and additional lipid materials that are sensitive to heat.

For some compositions, particularly cosmetics, it would be advantageous to add proteinaceous materials to the formulation to derive property improvements that are unrelated to the known abilities of proteins to emulsify fats and oils. Proteins or proteinaceous materials can either be co-cooked with the starch or blended with the starch after it exits the cooker. It may also be advantageous to add oils commonly used for cosmetic formulations, including coconut oil, silicone oil and jojoba oil.

It is also within the ambit of the invention to incorporate various hydrocolloid gums into the compositions of the invention. The hydrocolloids of principal interest are the natural gums. These are plant or microbial polysaccharides or their derivatives that can be readily dispersed in either cold or hot water to produce viscous solutions [R. L. Whistler, In Encyclopedia of Polymer Science and Technology, vol. 11, page 403 (1969)]. Examples of natural gums that are widely used industrially are the seaweed polysaccharides such as carrageenan, the pectins (derived mainly from citrus fruits), the exudate gums such as gum arabic and tragacanth, the seed gums such as guar and locust bean, the microbial polysaccharides such as xanthan, other gums such as tara and konjac and certain polysaccharide derivatives such as carboxymethyl cellulose (CMC) maltodextrins and corn syrup solids. The hydrocolloid can either be blended with the starch prior to jet cooking, or it can be added after the cooking step.

For some end-use applications, the dispersions of starch, active agent and water resulting from jet cooking may be used as is without further processing. However, for other applications it would be desirable for the dispersions to be dried and marketed as substantially dry powders. Although drying may be carried out by any method known to those skilled in the art, drum drying is the preferred method. Typical drum drying conditions for starch/active agent compositions are 20-60 psig within the drums with a drum rotation of 2-6 rpm. Preferred conditions are about 30 psig steam pressure within the drums and a drum rotation rate of 4 rpm. For purposes of this invention, a composition is considered to be dry when its moisture (free water) level is less than about 20%. Typically, the recovered products will be dried to about 5-12% moisture. Dry compositions may then be ground, milled, or pulverized to any desired particle size. It would be appreciated by the person skilled in the art that other methods of drying, such as spray drying or fluidized bed drying, could be used. Dried products can then be easily redispersed in water by high shear mixing to yield the useful aqueous compositions of this invention. To get the maximum redispersability of the dried products when added back to water, it is preferred that the jet-cooked material not be cooled below the retrogradation temperature of the starch.

As previously stated, the dried compositions of this invention have unique properties which can be tailored to specific end uses by appropriate selection of the ingredients, proportions, and processing conditions. For the most part, these compositions hydrate rapidly and yield dispersions that are not only smooth and viscous, but also possess considerable lubricity.

The active-containing compositions of the invention tend to have a non-greasy, yet slippery consistency. As such, they may be readily formulated as lotions, creams, gel, sticks, powders and the like. They may also be formulated in combination with vitamins, antibiotics, antifungal agents etc. When the compositions of the invention are formulated for topical human sunscreen applications, the total level of neat sunscreen agent in these preparations will typically be on the order of about 0.1 to 20%, by weight, and preferably within the range of about 1 to about 15%, by weight. The amount of sunscreen agent currently approved in the United States for inclusion in a topical skin treatment formulation is 15% by weight. It is contemplated that the agents of this invention will be incorporated into formulations that are both effective and safe. An effective amount (or photoprotective amount) is that amount which is sufficient to significantly induce a positive effect of protection against UV sunlight as compared to a control. One measure of the effectiveness of the sunscreen agent is the Sun Protection Factor (SPF) of the composition. SPF is a commonly used measure of photoprotection of a sunscreen against sunburn. The SPF is defined as the ratio of the UV energy required to produce minimal erythema on protected skin to that required to produce the same minimal erythema on unprotected skin in the same individual (see Federal Register, 43, no. 166, pp. 38206-38269, Aug. 25, 1978). A safe amount is that which does not produce serious side effects.

Other components that may be included in the sunscreen formulations of the invention include: other UVA and UVB sunscreen agents, such as 2-phenyl-benzimidazole-5-sulfonic acid, TEA salicylate, octyl dimethyl PABA, padimate-O (2-ethylhexyl 4-(dimethylamino) benzoate) and octyl methyl cinnamate; inorganic physical sunblocks, such as zinc oxide and $TiO_2$; artificial tanning agents; abrasives; absorbents; fragrances; pigments; colorings/colorants; essential oils; skin sensates; astringents, carriers and vehicles; thickening/structuring agents; emollients; emulsion stabilizers; excipients and auxiliaries commonly incorporated into cosmetic formulations; humectants; moisturizers; skin conditioners; anti-caking agents; antifoaming agents; antimicrobial agents; antioxidants; binders; buffering agents; bulking agents; chelating agents; chemical additives; film formers; humectants; opacifying agents; skin-conditioning agents; vitamins; and the like. Suitable emulsifiers include any of those conventionally used for cosmetic formulations, including for example, ethoxylated esters of natural derivatives, such as polyethoxylated esters of hydrogenated castor oil, a silicone oil emulsifier such as silicone polyol, free or ethoxylated fatty acid soap, an ethoxylated fatty alcohol, a free or ethoxylated sorbitan ester, an ethoxylated fatty acid or an ethoxylated glyceride. Exemplary agents and additives that could be included in formulations comprising the active agents of the invention, as well as suggested levels of addition, are given in U.S. Pat. No. 5,989,528 (Tanner et al.), which is herein incorporated by reference.

In the biocontrol delivery art, the sunscreen-containing compositions of the invention could be formulated with, and be protective of, antifungal agents, herbicides, nematocides, growth regulators, hormones, nutrients, germination stimulators, as well as insecticidal and herbicidal biological agents such as rhizobia, and other active agents as known in the art. Typically, these formulations would be in aqueous, sprayable form that would yield uniform films upon application to plants or other surfaces. Other applications of the compositions of the invention include paints and coatings and the like.

It is understood that any component, compound, material, agent, additive or the like (hereafter referred to as "secondary agent") such as those mentioned above, could be formulated with the compositions of the invention comprising the primary active agent at any stage of processing, provided that the secondary agent would be substantially stable under the conditions of processing (e.g. jet cooking). The person of ordinary skill in the art would be able to ascertain the point of processing at which it would be most advantageous to blend the secondary agent with the other components of the composition. If the secondary agent is an oil or other water-immiscible material, it could be introduced into the processing stream together with the primary active agent, or at any other time prior to jet-cooking; and would become incorporated into the starch composite in similar fashion as the primary active agent as described above.

As previously indicated, the delivery system of the invention permits the use of a lower level of sunscreen agent for comparable UV protection than if the agent were used alone.

The following examples are intended to further illustrate the invention, without any intent for the invention to be limited to the specific embodiments described therein. For example, thin films (0.30 to 3.00 $mg/cm^2$) of the compositions of this invention employing FAG as the agent exhibited 40-55% reductions in irradiance ($W/m^2$, 300 to 400 nm) compared to thin films of pure FAG of equal weight.

All references disclosed herein or relied upon in whole or in part in the description of the invention are incorporated by reference in their entirety.

EXAMPLES

Materials and Processing Equipment

The materials used in the examples, below, were obtained as indicated. Novozym 435 was obtained from Novozymes North America (Franklinton, N.C.). Pure Wesson brand soybean oil (SBO) was obtained from a local grocery store. Ethyl ferulate (ethyl 4-hydroxy-3-methoxycinnamate, EF) was purchased from Shanghai OSD (Shanghai, China). Genu pectin DD-slow set Z was obtained from CP Kelco (Atlanta, Ga.). Waxy cornstarch (Waxy No. 1) was obtained from A.E. Staley Mfg. Co. (Decatur, Ill.). All other reagents and solvents were purchased from Sigma-Aldrich (St Louis, Mo.).

The jet-cooker was a system comprising a Moyno® progressing cavity pump (Robbins Meyers, Springfield, Ohio, USA), a Penick and Ford hydroheater (Penford Corp, Cedar Rapids, Iowa, USA), a back pressure valve, and a flash tube for separating excess steam from the cooked starch. Shear/stirring was conducted in a stainless steel Waring® blender (Model 37BL84; Dynamics Corporation of America, New Hartford, Conn.). Drying was conducted on a pilot-scale double drum dryer (Model 20, Drum Dryer and Flaker Company, South Bend, Ind.), and milling was performed on a Retsch® centrifugal grinder (Brinkman Instruments Inc., Des Plains, Ill., USA).

Example 1

FAG Synthesis

A packed-bed bioreactor synthesis of FAG was prepared as described by Laszlo et al. (2003). A solution of EF (40 g) dissolved in SBO (160 g) was circulated over a bed of Novozym 435 (34 g) at 60° C. for 144 h. Byproducts and unreacted starting material were removed by molecular distillation at 120° C.

Example 2

SB-SBO and SB-FAG Composites

A mixture of waxy starch (400 g; moisture content approximately 10%) containing pectin (20 g) was added to deionized water (1500 mL) and stirred in a stainless steel Waring® blender (model 37BL84; Dynamics Corporation of America, New Hartford, Conn.). The resulting slurry was delivered to the jet cooker utilizing the Moyno® pump at a flow rate of about 1 L/min. The starch slurry and steam were combined in the hydroheater. Cooking temperature was 140° C. using steam supplied at 65 psig (448 kPa), and the hydroheater backpressure set at 40 psig (275 kPa). About 2000 mL of the starch solution (solids content: 17-18%, as determined by freeze-drying accurately weighed amounts of the solution in duplicate) was collected. FAG (197 g) was added to the starch solution (1000 g) and the mixture blended at high speed in a Waring® blender for approximately 1 min. This starch-oil suspension was then fed through the jet cooker under the conditions described above. Approximately 1900 mL of white, opaque dispersion was collected and allowed to cool in the dark to obtain the SB-FAG dispersion having a solids content of 12%-13%. The solids content varied between experiments due to dilution of the cooked dispersion with variable amounts of condensed steam. The aqueous SB-FAG dispersions were drum dried on the double drum dryer heated with steam at 206.8 kPa (135° C.). The flake-like product was then milled by passing it through the Retsch® centrifugal grinder to yield a flowable powder.

The flowable powder prepared above was easily redispersed in warm water using a Waring® blender. Both the resultant SB-FAG composites produced by jet cooking and the redispersed drum-dried composites gave smooth uniform dispersions that were similar in their physical characteristics to starch-soybean oil composites routinely prepared in our laboratories (Fanta et al., 1999). Freshly prepared aqueous SB-FAG dispersions containing 50% FAG had a pH ranging between 3.6 and 4.0 and a viscosity of 196 cps. Upon standing for three months, the viscosity was found to increase to approximately 300 cps. By light microscopy, (data not shown), the aqueous dispersions consisted of SB-FAG microdroplets ranging in size from 1 to 10 μm that did not coalescence over time. These SB-FAG composites are an effective method to carry FAG into aqueous media without the use of surfactants or stabilizers.

Example 3

FAG Films

FAG films were formed by dissolving 5 to 30 mg of FAG as prepared in Example 1 in ethanol (1 mL) and dispensing the solution into 5 cm dia. polished quartz crystal dishes (Quartz Scientific, Inc., Fairport Harbor, Ohio) then allowing the solvent to evaporate in air at room temperature for 24 h, protected from light.

Example 4

SB-FAG Films

SB-FAG films were formed by dispensing the aqueous SB-FAG dispersions as prepared in Example 2 across the top of 4.5×4.5 cm² polished quartz crystal slides (Quartz Scientific, Inc.) and drawing the dispersion across the slide to form a thin coating using a wet film applicator rod (Paul N. Gardner Company, Inc., Pompano Beach, Fla.) having a 0.005" (0.127 mm) film path thickness. The slides were placed under a box to exclude light while the water was removed by evaporation in air at room temperature for 16 h. The coverage (mg/cm²) of the FAG and SB-FAG films was determined by the weight difference of the dishes and slides before and after film formation. Desiccation of the films over calcium carbonate did not appreciably alter the weight of the films.

Example 5

Viscosity Measurement

The viscosity was measured at 25° C. using a Brookfield Model LVT viscometer (No. 2 spindle) operating at 60 rpm. The dispersions were gently shaken prior to viscosity measurement and triplicate measurements were made and an average value was calculated.

Example 6

Scanning Electron Microscopy

Aqueous SB-FAG dispersions were poured onto glass Petri dishes and allowed to air-dry into thin films. The films were removed from the dishes and fractured to expose the internal structure, then extracted in 100% ethanol for 16 h. Extracted samples were attached to aluminum SEM stubs using conductive tape so the fractured surface could be viewed, sputter-coated with gold-palladium, then examined utilizing a Jeol 6400 V scanning electron microscope operating at an accelerating voltage of 15 kV. FIG. 1 shows detailed SEM micrographs of these oil extracted fracture surfaces for an SB-FAG film that contained approximately 50 parts of FAG per 100 parts of waxy starch. As can be seen, removal of the FAG by the ethanol extraction left voids in the fractured surface where the FAG microdroplet domains resided. Also, it can be seen that the FAG is uniformly dispersed throughout the starch water phase as droplets ranging in size of approximately 1 to 10 μm. The shape of the voids is indicative of the spherical shape of the microdroplets and the smooth texture within the voids is consistent with the accretion of starch onto the smooth surface of the FAG oil droplets.

Example 7

Transmittance

It was necessary to determine if FAG maintained their UV absorbing efficacy after being subjected to the extreme temperature, pressure and shear conditions produced during the jet cooking process and while being formulated into a starch matrix. Thin films of FAG and SB-FAG were formed on polished quartz crystal slides. The FAG films were translucent while the SB-FAG films were slightly opaque. The transmittance of ultraviolet radiation (300 to 400 nm) through FAG and SB-FAG films was measured using a Heraeus Suntest® CPS Xenon lamp (Kendro Laboratory Products, Asheville, N.C.) set to simulate the energy experienced at 12:00 pm in central Illinois during summer sun exposure and a portable LI-1800 Spectroradiometer (LI-COR Biosciences, Lincoln, Nebr.). The transmittance ($T=P/P_o$) was calculated as the ratio of the power of UV radiation transmitted through the films (P, mV) to the power of UV radiation transmitted through air ($P_o$, mV). The irradiance (E, W/m²) of the transmitted UV radiation through the films was calculated by integration of the area under the transmittance curves. Irradiance values presented herein are the average of multiple films (n≧3) of the same coverage. The transmittance and irradiance data were baseline corrected for the quartz crystal plates and slides (T=0.99).

Figure 2:
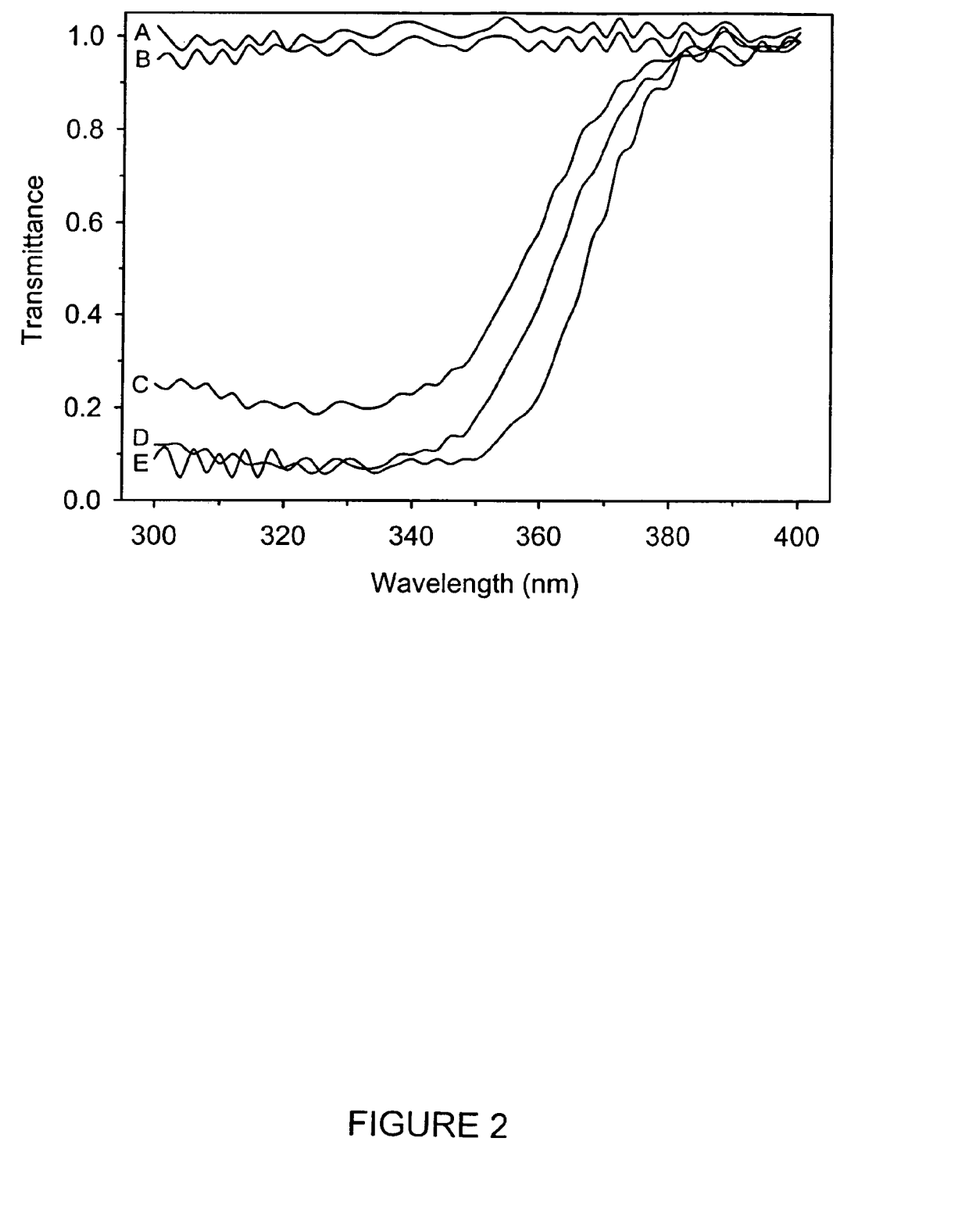
FIG. 2 are transmittance spectra of FAG and SB-FAG films on quartz slides compared to control films. The spectra were obtained after less than 1 min exposure to a xenon lamp (300 to 400 nm). The films and their coverage (mg/cm$^2$) on the quartz slides: (A) SBO, 1.38 mg/cm$^2$ (B) SB-SBO composite (51%, w/w oil/starch), 1.05 mg/cm$^2$; (C) FAG, 0.35 mg/cm$^2$; (D) FAG, 0.65 mg/cm$^2$; (E) SB-FAG composite (52%, w/w oil/starch), 0.68 mg/cm$^2$.

The transmittance of UV radiation through FAG and SB-FAG films is shown in FIG. 2. It should be noted that UVB and UVA radiation ranges between 290 and 400 nm, but due to the limit of the detector the transmittance could only be measured from 300 nm. Examination of the transmittance spectra of the FAG and SB-FAG films, however, shows that the absorption of UV radiation from 290 to 300 would likely not decrease appreciably. The data also shows that the UV absorbance of the SB-FAG films resulted from the FAG in the composite and not the starch, since the starch-based SBO (SB-SBO) control films permitted almost complete transmittance of the UV radiation. Unexpectedly, we found that encapsulating FAG into the starch matrix enhanced the UV absorbing ability of the FAG. This enhancement was clearly seen when the UV transmittance between the 0.68 mg/cm² SB-FAG film and the 0.35 mg/cm² FAG film were compared (FIG. 2, curves C and E). Although the SB-FAG film had a higher UV absorbance, the SB-FAG composite contained ca. 1:1 oil to starch ratio (w/w), so the amount of FAG coverage provided by the SB-FAG was actually 0.35 mg/cm². Thus, the UV absorptivity of a given quantity of FAG can be increased by formulating it into the starch matrix. The amount of FAG in the control film had to be doubled to 0.65 mg/cm² to obtain the same UV absorbance as the SB-FAG film (FIG. 2, curves D and E). These results confirmed that FAG not only survived the steam jet cooking processes, but the resulting SB-FAG composite films also enhanced the UV absorptivity relative to neat FAG films.

Example 8

FAG and SB-FAG UV Absorbing Stability

Figure 3:
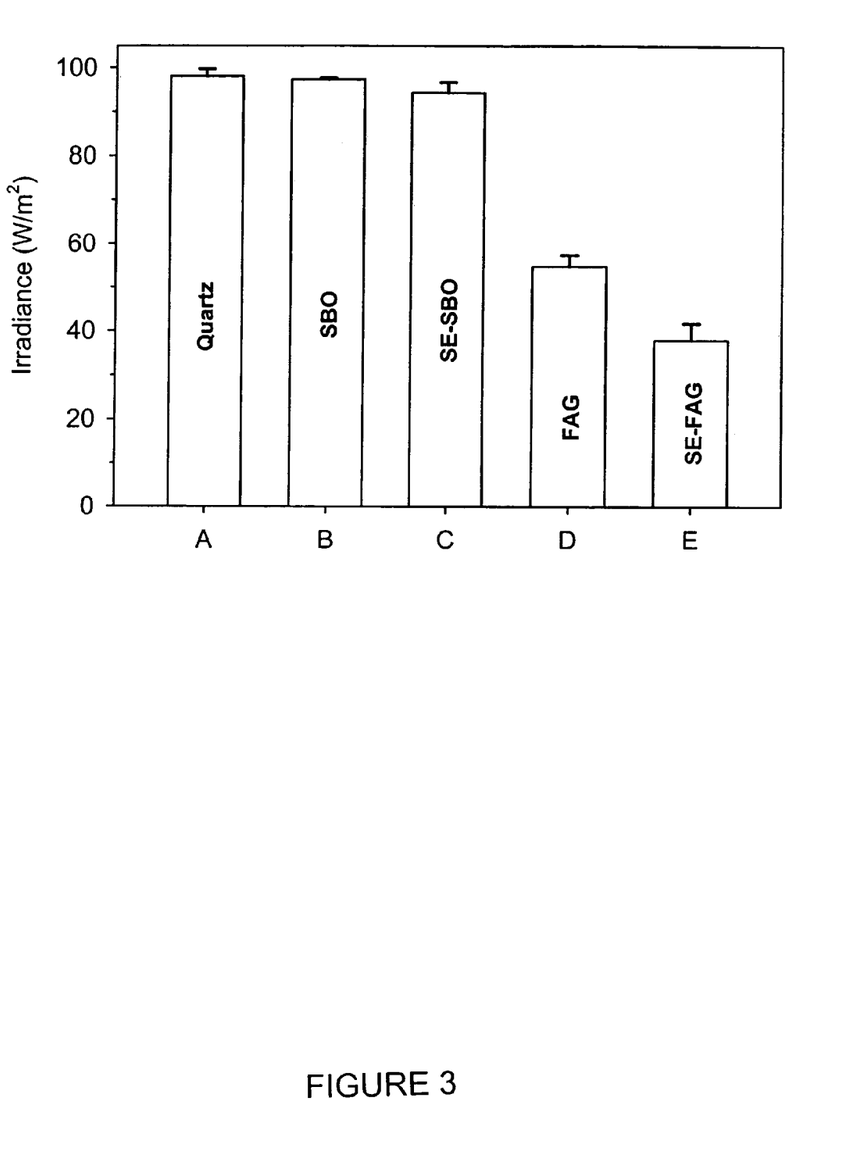
FIG. 3 illustrates irradiance through FAG and SB-FAG films on quartz slides compared to control films. The irradiance was obtained after less than one minute exposure to a xenon lamp (300 to 400 nm). The values reported are the means of n≧3 films, and the bars indicate standard deviations. The films and their coverage (mg/cm$^2$) on the quartz slides: (A) quartz slide; (B) SBO, 1.39 mg/cm$^2$; (C) SB-SBO composites (51%, w/w oil/starch), 1.74 mg/cm$^2$; (D) FAG, 0.23 mg/cm$^2$; (E) SB-FAG composites (51%, w/w oil/starch), 0.32 mg/cm$^2$.

To investigate the UV absorbing stability of the FAG and the SB-FAG films over time it was more convenient to compare the irradiance values of the films. The irradiance, the energy transmitted to a surface per unit area (W/m²), was obtained by integrating the transmittance spectrum of a film. FIG. 3 compares the initial irradiance values, less than one minute UV (300 to 400 nm) exposure, of SB-FAG films to control films and a blank quartz slide. The irradiance values reported are the mean of $n \geq 3$ films, and the standard deviations are represented by error bars. Lower irradiance values correspond to greater UV absorbance. The quartz slide allows the complete transmittance of UV radiation (T=0.99) over the entire 300 to 400 nm range, and this corresponds to an irradiance of 98.0 W/m², the highest value possible in our experiments. As the irradiance data shows, SBO and the SB-SBO films have very similar values compared to the quartz slide (FIG. 3). Thus, the effective UV absorbance of SBO and the starch matrix was negligible. The unexpected improvement in the SB-FAG film absorptivity (37.4 W/m² at 0.32 mg/cm²) relative to the FAG film (54.2 W/m² at 0.23 mg/cm²) was readily seen by comparison of their irradiances. Because the SB-FAG films used in these experiments contained ca. 50% (w/w) FAG to starch, the actual FAG coverage provided by the SB-FAG films was only 0.16 mg/cm². Therefore, the SB-FAG films contained 30% less FAG than the neat FAG control films, but produced a 16.8 W/m² lower irradiance value. These data, again, illustrate the synergistic effect between the starch and FAG in the SB-FAG composites to improve the UV absorbing efficacy of FAG.

Figure 4:
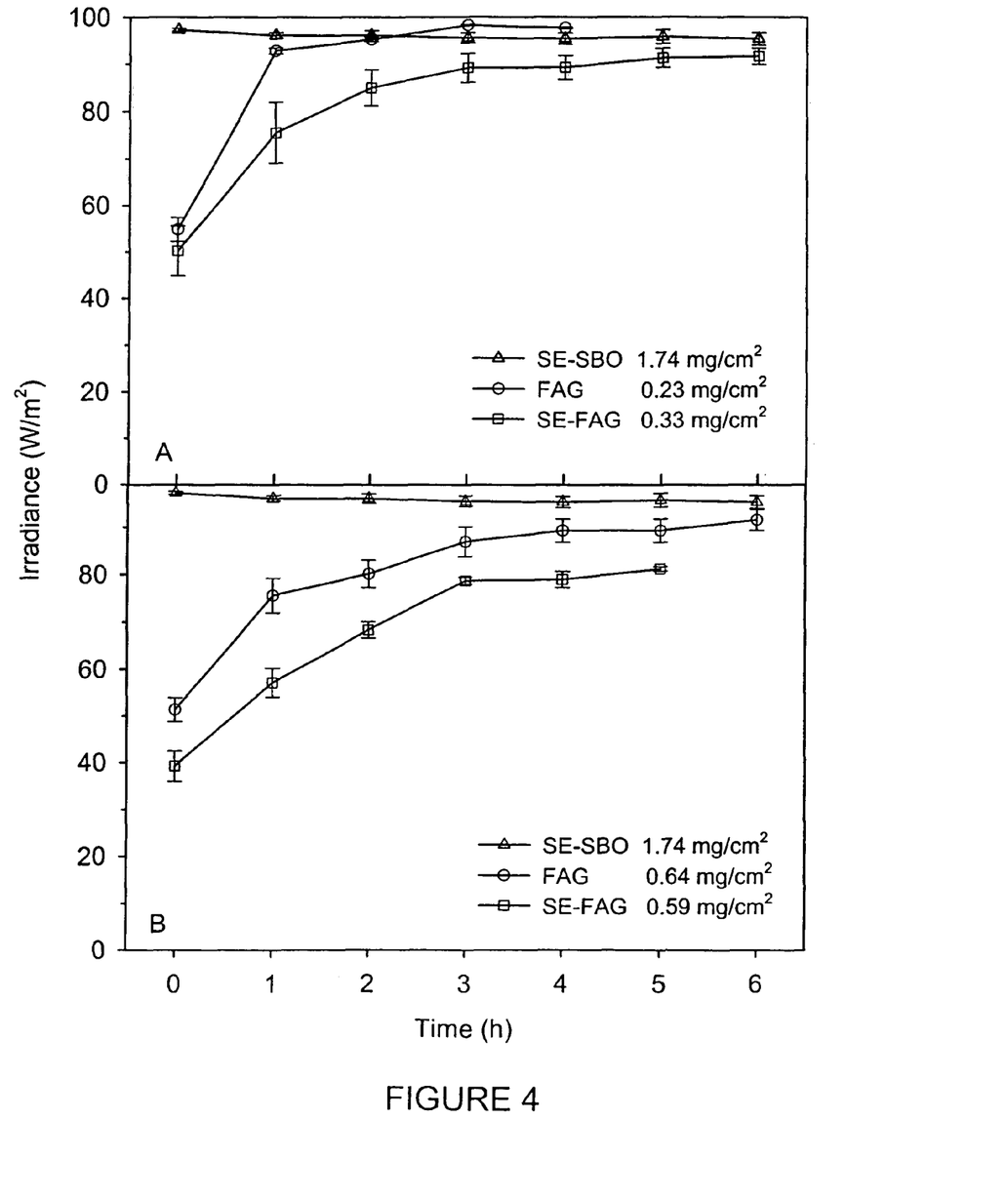
FIGS. 4A and 4B illustrate irradiance through FAG and SB-FAG films on quartz slides over time. The irradiance was obtained by exposure to a xenon lamp (300 to 400 nm). The irradiance values reported are the means of n≧3 films, and the bars indicate standard deviations. The films and their coverage (mg/cm$^2$) on the quartz slides.

In addition to improving the initial UV absorptivity of FAG, microencapsulating the FAG into the starch matrix prolonged the FAG efficacy over time. FIG. 4A shows that at a surface coverage of 0.23 mg/cm², neat FAG quickly lost its UV absorptivity within 1 h of exposure to the UV radiation, rendering it as efficacious as the SB-SBO control film. However, when FAG was applied at a surface coverage of 0.33 mg/cm² as a SB-FAG composite containing 48% FAG its UV absorbance was extended for more than 4 h before it degraded to the irradiance of the SB-SBO control. The superior UV stability of the SB-FAG films was even more pronounced at higher coverages (FIG. 4B). It is necessary to stress that the SB-FAG films contained 30% and 50% less FAG than the corresponding neat FAG (FIGS. 4A and 4B, respectively). This shows that formulation of FAG within the starch matrix resulted in half the quantity of FAG providing equal or better UV stability over time compared to the non-formulated FAG.

Example 9

SB-FAG 10% and 25% Composites and a SB-FAG 50% composite containing Corapan TQ A mixture of waxy starch (401.1 g; moisture content=10.8%) containing pectin (20.8 g) was added to deionized water (1200 mL) and stirred in a stainless steel Waring® blender. The resulting slurry was delivered to the jet cooker utilizing a Moyno® progressing cavity pump at a flowrate of about 1 L/min. The starch slurry and steam were combined in a Penick and Ford hydroheater. Cooking temperature was 140° C. using steam supplied at 65 psig (448 kPa), and the hydroheater backpressure set at 40 psig (275 kPa). 2050 mL of the starch solution (solids content: 17-18%, as determined by freeze-drying accurately weighed amounts of the solution in duplicate) was collected. FAG at three different levels (10% composite=4.5 g FAG; 25% composite=15.6 g FAG; 53% composite=51.3 g FAG that contained 4.47 g Corapan TQ [8.7 wt % Corapan TQ]) was added to the hot starch solutions (10% composite=251.4 g; 25% composite=251.8 g; 53% composite=252.3 g) and each mixture blended at high speed in a Waring® blender for 5 minutes. After blending, a white opaque dispersion was collected for each preparation and these were allowed to cool in the dark to obtain the SB-FAG dispersion having a solids content of 10%-21%. The aqueous SB-FAG dispersions were then utilized to prepare films of each sunscreen-starch composite which were subsequently utilized in transmittance and irradiance experiments.

We claim:

1. A composition comprising droplets of a cinnamate-modified vegetable oil stably and substantially uniformly distributed in a continuous starch phase in the absence of an external emulsifier, wherein said starch phase consists essentially of completely disrupted starch granules and said droplets are surrounded by a boundary layer separating them from the starch phase.

2. The composition of claim 1, wherein said cinnamate-modified vegetable oil is characterized by the structural formula:

wherein at least one of $R_1$, $R_2$, or $R_3$ is a feruloyl, coumaroyl, sinapoyl, or o-methylsinapoyl moiety; or wherein at least one of $R_1$, $R_2$, or $R_3$ is an acyl moiety modified with one or more feruloyl, coumaroyl, sinapoyl, or o-methylsinapoyl moiety; and wherein the each of the remaining positions of $R_1$, $R_2$ and $R_3$ is selected from the group consisting of C2-C26 acyl moiety, C1-C26 aliphatic moiety, and hydrogen.

3. The composition of claim 2, wherein at least one of $R_1$ and $R_2$ is a feruloyl moiety and wherein the each of the remaining positions of $R_1$, $R_2$ and $R_3$ is selected from the group conisting of C2-C26 acyl moiety, C1-C26 aliphatic moiety, and hydrogen.

4. The composition of claim 1 wherein said composition is an aqueous dispersion.

5. The composition of claim 1 wherein said composition is a dried solid.

6. The composition of claim 1 wherein said starch is selected from the group consisting of cornstarch, wheat starch, rice starch, potato starch, and tapioca starch.

7. The composition of claim 1 wherein the starch:cinnamate-modified vegetable oil weight ratio is in the range of 1:1 and 9:1.

8. The composition of claim 1 wherein the starch:cinnamate-modified vegetable oil weight ratio is in the range of about 1:1 to 3:2.

9. The composition of claim 1 wherein said droplets have a maximum diameter of about 100 microns.

10. The composition of claim 1 wherein 95% of said droplets have a diameter of less than about 10 microns.

11. A formulation comprising the composition of claim 1 wherein the formulation is selected from the group consisting of UV-protective sunscreen agents, antioxidants, skin care agents and cosmetics wherein said cinnamate-modified vegetable oil is present in said formulation in a amount of 0.1-20% by weight.

12. A method of preparing a composition characterized by a uniform and stable distribution of cinnamate-modified vegetable oil throughout a continuous starch phase, the method comprising the following steps;
   a. cooking an aqueous dispersion of starch under conditions which will completely solubilize the starch;
   b. maintaining the completely solubilized starch in a non-retrograded state and combining an aqueous solution thereof with said cinnamate-modified vegetable oil under conditions of sufficient turbulence to produce a dispersion comprising droplets of said cinnamate-modified vegetable oil uniformly dispersed throughout the aqueous starch solution, wherein said cinnamate-modified vegetable oil is either co-cooked with the starch or combined with the starch after cooking to form the dispersion; and
   c. recovering the resultant dispersion under conditions which stabilize the distribution of the cinnamate-modified vegetable oil in the starch phase.

13. The method of claim 12, wherein said cooking in step (a) is excess steam jet cooking.

14. The method of claim 13, wherein said excess steam jet cooking comprises passing said aqueous dispersion of starch and said cinnamate-modified vegetable oil through an excess steam jet cooker two times.

15. The method of claim 12, wherein said recovering in step (c) comprises drum-drying the emulsion prior to retrogradation of the starch.

16. A product produced by the process of claim 12.

17. The composition of claim 1, wherein said cinnamate-modified vegetable oil comprises a feruloylated acylglycerol of the structural formula:

wherein $R_1$ is feruloyl, $R_2$ is H, and $R_3$ is a $C_2$-$C_{26}$ acyl.

18. The method of claim 12, wherein said cinnamate-modified vegetable oil comprises a feruloylated acylglycerol of the structural formula:

wherein $R_1$ is feruloyl, $R_a$ is H, and $R_x$ is a $C_2$-$C_{26}$ acyl.

* * * * *